Figure 1:
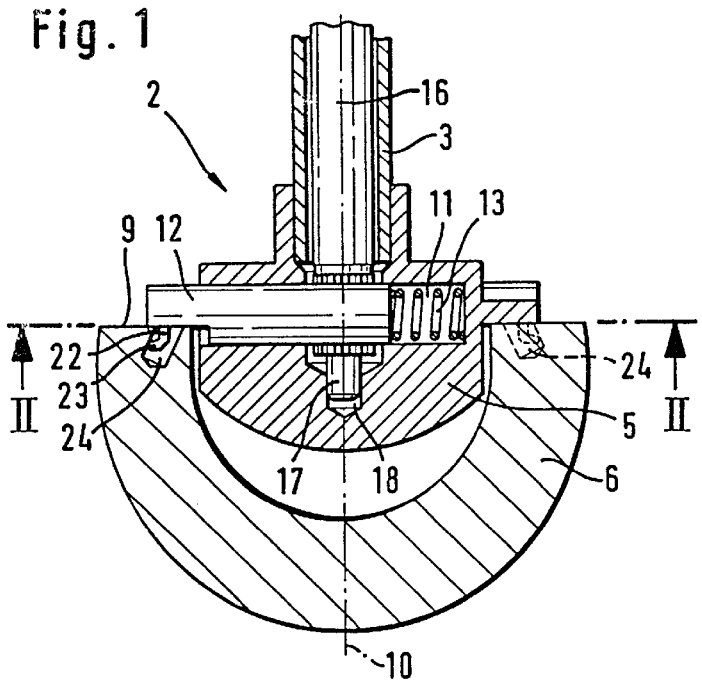

United States Patent
Keller

[11] Patent Number: 5,928,287
[45] Date of Patent: Jul. 27, 1999

[54] ACETABULAR CUP AND SURGICAL INSTRUMENT FOR IMPLANTING SAME

[75] Inventor: Arnold Keller, Kayhude, Germany

[73] Assignee: Waldemar Link (GmbH & Co.), Germany

[21] Appl. No.: 08/981,647
[22] PCT Filed: May 9, 1997
[86] PCT No.: PCT/EP97/02399
  § 371 Date: Jan. 7, 1998
  § 102(e) Date: Jan. 7, 1998
[87] PCT Pub. No.: WO97/42915
  PCT Pub. Date: Nov. 20, 1997

[30] Foreign Application Priority Data

May 9, 1996 [DE] Germany ............ 29608453 U

[51] Int. Cl.$^6$ ............ A61B 17/58; A61B 17/16
[52] U.S. Cl. ............ 623/22; 606/91; 623/18
[58] Field of Search ............ 623/22, 18; 606/73, 606/81, 91

[56] References Cited

U.S. PATENT DOCUMENTS

| | | | |
|---|---|---|---|
| 4,023,572 | 5/1977 | Weigand et al. | 128/305 |
| 4,856,503 | 8/1989 | Schelhas | 128/92 VJ |
| 5,059,196 | 10/1991 | Coats | 606/91 |
| 5,112,338 | 5/1992 | Anspach, III | 606/99 |
| 5,116,339 | 5/1992 | Glock | 606/91 |
| 5,171,313 | 12/1992 | Salyer | 606/86 |
| 5,236,433 | 8/1993 | Salyer | 606/91 |
| 5,364,403 | 11/1994 | Peterson | 606/91 |
| 5,501,686 | 3/1996 | Salyer | 606/86 |
| 5,540,697 | 7/1996 | Rehmann | 606/99 |
| 5,571,200 | 11/1996 | Cohen | 606/81 |
| 5,658,294 | 8/1997 | Sederholm | 606/91 |
| 5,683,399 | 11/1997 | Jones | 606/91 |

FOREIGN PATENT DOCUMENTS

| | | | |
|---|---|---|---|
| 0 303810 | 7/1988 | European Pat. Off. | |
| 0 453694 | 4/1990 | European Pat. Off. | |
| 2281095 | 5/1976 | France | |
| 2663840 | 1/1992 | France | A61F 2/46 |
| 2676172 | 11/1992 | France | |
| 2721502 | 12/1995 | France | A61F 2/46 |
| WO 94/21199 | 9/1994 | WIPO | A61F 2/46 |
| WO 95/11641 | 5/1995 | WIPO | A61F 2/46 |

*Primary Examiner*—David H. Willse
*Assistant Examiner*—Suzette Jackson
*Attorney, Agent, or Firm*—Medlen & Carroll, LLP

[57] ABSTRACT

Arrangement consisting of an acetabular cup prosthesis and of an implantation instrument for same. The acetabular cup prosthesis has at least one undercut holding recess in its edge end face. The instrument has a block which fits with centring into the opening or onto the opening edge of the acetabular cup prosthesis, and at least one holding projection positionally assigned to the holding recess and fitting into the latter, which holding projection is movable transverse to the opening direction, can be locked in a position in which it catches in the undercut of the holding recess, and can be withdrawn therefrom by means of an actuating member.

22 Claims, 1 Drawing Sheet

U.S. Patent

Jul. 27, 1999

5,928,287

ACETABULAR CUP AND SURGICAL INSTRUMENT FOR IMPLANTING SAME

For implanting acetabular cup endoprostheses into the acetabulum, which may optionally have been provided with a bed of cement, instruments are normally used which have, at the end of a gripping rod, a holding head which, for the purpose of holding the cup in a predetermined relative position to the instrument, has a block, engaging in the matching cavity of the cup, and a collar which bears on the edge of the cup. The force necessary for pressing the cup into the acetabulum can thereby be transmitted easily to the cup. However, it is desirable that the cup is also held securely on the instrument in the opposite force direction and in the direction of rotation, and that it can be released from the instrument again without transmitting appreciable forces.

For this purpose, a known implantation instrument (FR-A-2,721,502), on which the wording of the preamble of claim 1 is based, has a block which grips in the acetabular cup and which is adapted exactly to the shape of the opening forming the cavity, and holding pins which are arranged axially parallel on the collar and engage in holding openings which are designed as axially parallel bores on the front face of the acetabular cup. The latter is held on the instrument via the block and the holding pins by means of frictional forces. For its removal, a plunger which is axially displaceable counter to a spring force by means of an actuating member forces the instrument off from the acetabular cup. The disadvantage is that the acetabular cup is held on the instrument only via the unreliable frictional engagement, which has to be made very powerful so that the desired holding force is obtained even in the event of the coming-together of most unfavourable tolerance deviations. For release, a comparatively great force, overcoming the holding force, must be applied, generally greater than the desired holding force. The greater the force that has to be applied for release, the more difficult it is to hold the instrument steady.

An implantation instrument which likewise holds the prosthesis by frictional force is known from U.S. Pat. No. 5,169,399. This comprises a head which is adapted to the shape of the cavity of the acetabular cup and whose halves are pressed away from each other and against the inner wall of the acetabular cup by a spring force. To release the instrument from the acetabular cup, the halves of the head are moved towards each other using an actuating lever, so that the contact with the acetabular cup is eliminated. In view of the low coefficient of friction of the inner face of an acetabular cup, the force with which the halves of the head of this implantation instrument are pressed against the inner face of the acetabular cup, and which has to be applied as releasing force when removing the instrument, must be greater than the desired holding force. The disadvantages of this device therefore correspond to those mentioned above. In addition to this, there is only unsatisfactory protection against unwanted turning of the acetabular cup on the instrument.

In the case of another known implantation instrument (WO94/21199), radially arranged holding projections engage in holding openings on the inner side of the acetabular cup. An intermediate piece is attached to the instrument, the latter having a block fitting with centering in an opening in the base of the prosthesis, on which intermediate piece there are holding projections which are movable transverse to the opening direction, engage with a spring force in the holding openings, and can be withdrawn from these by means of an actuating member. This arrangement is disadvantageous because the openings in the inner face of the prosthesis are generally undesirable and demand a greater wall thickness of the prosthesis at an anatomically unfavourable location.

For the purpose of holding acetabular cup reamers, instruments are known (U.S. Pat. No. 5,171,313, FR-2,281,095) which engage with radially arranged holding pins in openings on the inner side of a reamer head and which can be withdrawn counter to a spring force by means of an actuating member. The use of such instruments for holding implants would be disadvantageous for the reason mentioned in the previous paragraph.

In the case of an instrument for releasing implanted acetabular cup prostheses (U.S. Pat. No. 5,112,338), radially arranged holding projections engage in slots on the end face of the acetabular cup. Since the slots are open towards the front, it is not possible to hold the acetabular cup on the instrument.

For implanting a bearing dish for a joint cup which is anchored cementlessly in the acetabulum with the aid of spikes which are arranged on elastic tongues, an implantation instrument is known (EP-A-453,694) which is designed specially such that the tongues are drawn inwards during the implantation by the instrument, so that the spikes do not interfere with the implantation movement of the bearing dish to the desired position. When this position has been reached, the tool is released, so that the tongues once again assume the outer position and the spikes penetrate the surrounding tissue in order to fix the bearing dish in place. Since the tongues, and the openings cooperating with the instrument, are arranged deep in the bearing dish, the known arrangement does not provide any indication of how it is possible to avoid the engagement of the instrument in the cavity of the cup.

Starting from the instrument known from FR-A-2,721,502, the invention is based on the object of providing an arrangement which consists of implantation instrument and cup and in which the instrument engages on the end face of the cup and, nevertheless, allows reliably reproducible holding forces to be exerted, and in which the instrument can be easily released from the cup. The solution according to the invention lies in the features of claim 1.

The acetabular cup has in its edge end face at least one holding recess which is undercut in relation to the opening direction. The opening direction is that direction in which the acetabular cup opens out. It is also the direction in which the instrument is to be removed from the acetabular cup, based on the direction of the cooperating surface parts of instrument and acetabular cup. This is generally the direction normal to the plane in which the edge end face lies.

The instrument has a block which fits with centering into the opening or onto the opening edge of the acetabular cup. It additionally has at least one holding projection which is positionally assigned to the holding recess of the acetabular cup and accordingly can be introduced into the holding recess. It is designed such that it can engage in the undercut of the holding recess. It can be locked in this position. It can be withdrawn from the locked position by means of a special actuating member. Two or more holding projections and holding recesses are generally provided, distributed uniformly about the circumference so that their locking forces balance each other. The advantage of this arrangement lies in the fact that the acetabular cup is held securely on the instrument, even against application of substantial forces, so long as the locking of the holding projections in the holding recesses is not released, and that, however, after the locking has been released, no tensile forces whatsoever can any longer be exerted on the acetabular cup when removing the instrument from the latter. The locking need not be designed in the manner of a fixed lock, although this is possible; in general it is sufficient for the holding projections to be held in the locking position by a spring force, in which case the spring force is chosen to be so great that it is sufficient, under all practically occurring conditions, for holding the acetabular cup securely on the instrument.

The actuating member with which the locking is released is expediently arranged on a hand grip of the instrument at a location which is accessible in the normal gripping position. This is intended to allow the physician to release the instrument without altering his hand position. This avoids undesired relative movements being transmitted to the acetabular cup and inadvertently changing the position of the latter.

The holding projections of the instrument expediently run roughly in the opening direction and have a hook which is directed sideways (in relation to the principal direction of the holding projections) and which engages in the undercut of the openings. This embodiment is particularly simple if the holding recesses are designed as bores running at an angle relative to the opening direction, the angled inclination preferably running outwards or inwards in the radial direction. Accordingly, the hooks of the holding projections, and the direction of the locking movement of the holding projections, are also directed outwards or inwards.

The reliability of the engagement can be further enhanced by the bores being provided with a circumferential fluting, for example in the form of a thread. This is especially so when the lateral extension of the holding projection has an edge or several edges cooperating with the fluting.

So that the holding projections of the instrument can be moved transverse to the opening direction of the acetabular cup, they are expediently arranged on slide pieces which are guided in essentially radial slide guides in the tool head. A gear arrangement can be provided for their movement, this gear arrangement connecting the slide pieces to an actuating shaft which is mounted pivotably in a bar arranged centrally on the head and connecting the latter to the hand grip, and which actuating shaft bears the actuating member projecting laterally from the connecting bar. The locking spring can act on the slide pieces or engage on the actuating shaft.

Figure 3:
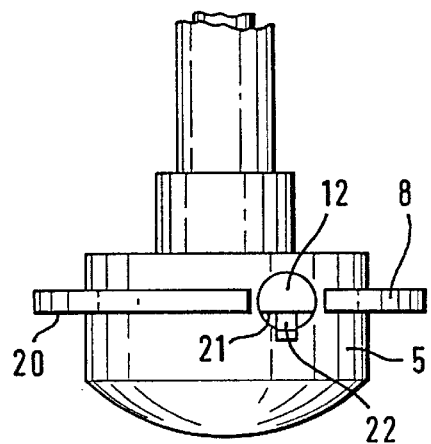
Figure 2:
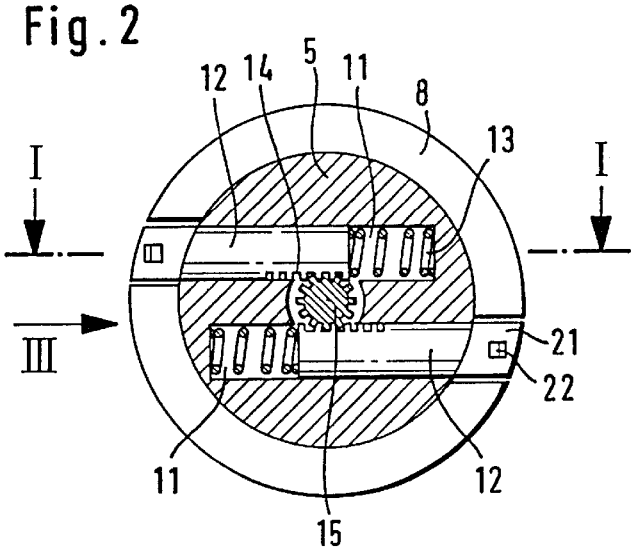
Figure 4:
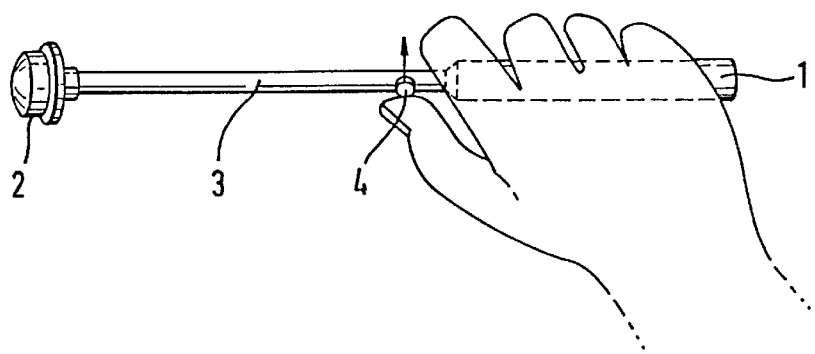

The invention is explained in more detail below, with reference to the drawing which represents an advantageous illustrative embodiment. In the drawing:

FIG. 1 shows the head of the instrument and an acetabular cup in longitudinal section along the line I—I in FIG. 2, FIG. 2 shows a cross-section through the head of the instrument along the line II—II in FIG. 1, FIG. 3 shows a side view of the instrument head in direction III in FIG. 2, and FIG. 4 shows an overall view of the instrument.

The instrument consists of the hand grip 1, the instrument head 2, and a bar 3 which connects these two parts and on which the actuating member 4 is arranged in such a way that, with the hand in a normal position, it can easily be actuated counter to a spring force, in the direction of the arrow, using one finger. By means of this actuation, the connection to the acetabular cup, previously held by the instrument, can be released.

The instrument head has a cylindrical block 5 whose diameter is dimensioned with a certain play matching the size and shape of the opening of the cup 6 and is fitted into the opening. It additionally has a collar 8 which is intended to be applied on the end face 9 of the cup 6. In this way the instrument is aligned with the opening direction 10 of the cup which, in the examples represented, coincides with the midline of the cup and of the instrument.

In the instrument head there are two bores 11 which lie parallel, with their midpoints symmetrical to each other, in a plane running perpendicular to the midline 10, and which each contain a slide piece 12 which is forced towards the outside by a spring 13. On their side facing the midline, the slide pieces 12 are designed as toothed racks 14 which cooperate with a centrally arranged pinion 15. The pinion 15 is arranged at the end of a shaft 16 which runs within the hollow bar 3 and is connected to the actuating member 4. At the outermost end, it is provided with a stud 17 which is mounted in a bore 18 of the instrument head. Along the rest of its course, the shaft is borne by the inner face of the bar 3. By actuating the actuating member 4 in the direction of the arrow shown in FIG. 4, the pinion is turned so that the slide pieces 12 are drawn back into the instrument head counter to the action of the springs 13. When the actuating member 4 is released, these parts take up the end position represented in FIG. 2.

In the embodiment represented, the slide pieces each have, in a plane 21 flush with the underside 20 of the collar 8, a holding projection 22 whose principal direction runs approximately parallel to the central axis 10 and which has, at the end, a hook 23 pointing approximately radially outwards. Bores 24 are provided in the end face 9 of the associated cup 6 at corresponding circumferential positions, which bores 24 run radially outwards, slightly obliquely, and in this way, as is represented in FIG. 1, form an undercut (in relation to the axis 10) into which the hook 23 can engage. For connecting the two parts, the slide pieces 12 are drawn back by actuating the actuating member 4. In their inner end position, the holding projections 22 are situated at approximately the same radial position as the openings of the bores 24. It is therefore easy to locate the position in which the instrument and the cup fit together so that the holding projections 22 can engage in the bores 24. The actuating member is then released; the slide pieces 12 slide approximately radially outwards, as a result of which the hooks 23 come into engagement with the undercut of the bores 24. The cup then sits securely on the instrument because the hooks 23 are locked in their holding position by the springs 13. The inclination of the bores 24 and the force of the springs 13 can be readily dimensioned in such a way that the holding force, with which the hooks 23 are locked in the holding position, is sufficient for every case of use which may reasonably arise. The holding force of the hooks 23 in the oblique bores 24 can be further improved by a fluting (for example a threaded section) of the bores. It will be understood that the spacing of the bores 24 from each other is not greater than the maximum distance between the hooks 23. Once the cup has been implanted or, for other reasons, has to be released from the instrument, the actuating member 4 is once again actuated; when actuated, the holding projections 22 draw radially back and the instrument can be removed from the cup without any disruptive forces being exerted on the latter.

The illustrative embodiment shows that the direction of movement of the holding projections 22 does not have to be exactly radial, but only needs to have a sufficient component of radial movement. Nor does the movement need to be executed rectilinearly; instead, it might possibly involve some kind of swivel movement.

I claim:

1. An apparatus comprising:

a) an acetabular cup prosthesis having a cavity and an end face, wherein said end face contains at least one undercut recess; and b) an implantation instrument having:
   i) a block capable of engaging said cavity of said acetabular cup,
   ii) at least one holding projection capable of engaging said at least one undercut recess of said acetabular cup, and
   iii) an actuator member capable of engaging and disengaging said acetabular cup and said implantation instrument, and wherein in a first position, said actuator member engages said at least one holding projection with said at least one undercut recess, and in a second position, said actuator member disengages said at least one holding projection from said at least one undercut recess.

2. The apparatus of claim 1, further comprising a spring capable of locking said at least one holding projection in said undercut recess.

3. The apparatus of claim 1, further comprising a hand grip, and wherein said actuator member is contained within said hand grip.

4. The apparatus of claim 1, wherein said implantation instrument further comprises a collar positioned parallel to the end face of said acetabular cup.

5. The apparatus of claim 1, wherein said at least one holding projections further comprises a hook.

6. The apparatus of claim 1, wherein said at least one recess is bored at an angle to the planes of said end face and said recess of said acetabular cup, to produce recessed bores.

7. The apparatus of claim 6, wherein said recessed bores further have a circumferential fluting.

8. The apparatus of claim 7, wherein said circumferential fluting comprises threads.

9. The apparatus of claim 1, wherein said implantation instrument further comprises a first radial slide guide, a second radial slide guide, a first slide piece, and a second slide piece.

10. The apparatus of claim 9, wherein said first and second radial slide guides are positioned on said block.

11. The apparatus of claim 10, wherein said first slide piece is positioned on said first slide guide, said second slide piece is positioned on said second slide guide, and said holding projections are arranged on said first and second slide pieces.

12. The apparatus of claim 11, wherein said implantation instrument further comprises a gear arrangement positioned between said slide pieces, and an actuating shaft pivotably mounted in a connecting bar positioned on said head, wherein said connecting bar connects said head to said actuator member.

13. An apparatus comprising:
   a) an acetabular cup prosthesis having a cavity and an end face, wherein said end face contains at least one undercut recess; and
   b) an implantation instrument having:
      i) a block capable of engaging said cavity of said acetabular cup,
      ii) at least one holding projection capable of engaging said at least one undercut recess of said acetabular cup, and
      iii) an actuator member capable of engaging and disengaging said acetabular cup and said implantation instrument,
      iv) a first slide piece positioned on a first slide guide, and a second slide piece positioned on a second slide guide,
      v) a gear arrangement positioned between said first and second slide pieces, and
      vi) an actuating shaft pivotably mounted in a connecting bar positioned on said head, wherein said connecting bar connects said head to said actuator member, and wherein in a first position, said actuator member engages said at least one holding projection with said at least one undercut recess, and in a second position, said actuator member disengages said at least one holding projection from said at least one undercut recess.

14. The apparatus of claim 13, further comprising a spring capable of locking said at least one holding projection in said undercut recess.

15. The apparatus of claim 13, further comprising a hand grip, and wherein said actuator member is contained within said hand grip.

16. The apparatus of claim 13, wherein said implantation instrument further comprises a collar positioned parallel to the end face of said acetabular cup.

17. The apparatus of claim 13, wherein said at least one holding projections further comprises a hook.

18. The apparatus of claim 13, wherein said at least one recess is bored at an angle to the planes of said end face and said recess of said acetabular cup, to produce recessed bores.

19. The apparatus of claim 13, wherein said recessed bores further have a circumferential fluting.

20. The apparatus of claim 19, wherein said circumferential fluting comprises threads.

21. A method for implanting an acetabular cup prosthesis into an acetabulum, comprising the steps of:
   a) providing the apparatus of claim 1, and an acetabulum,
   b) contacting said acetabular cup prosthesis with said implantation instrument in a manner such that said acetabular cup prosthesis is held on said implantation instrument; and
   c) contacting said acetabulum with said acetabular cup prosthesis held on said implantation instrument.

22. The method of claim 21, further comprising the step of disengaging said implantation instrument from said acetabular cup prosthesis, under conditions such that said acetabular cup prosthesis remains in contact with said acetabulum.

* * * * *